United States Patent
Scirica et al.

(10) Patent No.: US 6,264,605 B1
(45) Date of Patent: *Jul. 24, 2001

(54) SURGICAL INSTRUMENT

(75) Inventors: Paul Scirica, Huntington; Cathy Aranyi, Easton, both of CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/597,640

(22) Filed: Jun. 20, 2000

Related U.S. Application Data

(62) Division of application No. 09/236,311, filed on Jan. 22, 1999, now Pat. No. 6,102,853.
(60) Provisional application No. 60/072,405, filed on Jan. 23, 1998, and provisional application No. 60/105,364, filed on Oct. 23, 1998.

(51) Int. Cl.[7] .............................................. A61B 1/32
(52) U.S. Cl. ........................ 600/227; 600/229; 600/233
(58) Field of Search .................................... 600/229, 227, 600/201, 208, 233, 210, 231, 234, 235, 211, 232; 606/1

(56) References Cited

U.S. PATENT DOCUMENTS

| Re. 34,150 | 12/1992 | Santilli . |
|---|---|---|
| 497,064 | 5/1893 | Van Meter . |
| 1,157,202 | 10/1915 | McLeland . |
| 1,400,616 | 12/1921 | Pearson . |
| 1,707,689 | 4/1929 | Sloan . |

(List continued on next page.)

FOREIGN PATENT DOCUMENTS

| 0 246 086 A2 | 11/1987 | (EP) . |
|---|---|---|
| 0 336 526 A1 | 10/1989 | (EP) . |
| 0 791 329 A1 | 8/1997 | (EP) . |
| 0 791 330 A2 | 8/1997 | (EP) . |
| 0 792 620 A2 | 9/1997 | (EP) . |
| 1005345 | 7/1957 | (FR) . |
| 2102681 | 2/1983 | (GB) . |
| 116547 | 6/1918 | (IN) . |
| 938967 | 8/1980 | (RU) . |
| WO 89/04145 | 5/1989 | (WO) . |
| WO 92/21296 | 12/1992 | (WO) . |
| WO 95/17127 | 6/1995 | (WO) . |
| WO 97/10753 | 3/1997 | (WO) . |

OTHER PUBLICATIONS

"Pilling Surgical Instruments" brochure by Pilling, A Rusch International Company, 1993.

Borst, Corneliu, et al., "Coronary Artery Bypass Grafting Without Cardiopulmonary Bypass and Without Interruption of Native Coronary Flow Using a Novel Anastomosis Site Restraining Device ("Octopus")", Journal of the American College of Cardiology, vol. 27, No. 6, pp. 1356–1364 (May 1996).

*Primary Examiner*—Pedro Philogene

(57) ABSTRACT

A mounting assembly for mounting a surgical instrument to a base, which facilitates positioning a surgical instrument relative to the surgical site so that only the minimum portion of the instrument is positioned in the free space available around the surgical site. A surgical instrument is also provided which includes a handle, a tool member, and a segmented flexible articulating arm which operatively connects the handle and the tool member. Also provided is an instrumentation kit having a surgical instrument which includes an end effector connecting assembly disposed at the distal end portion of an articulating arm to facilitate the removal or attachment of and end effector from the distal end of the articulating arm. The surgical instrumentation kit also includes a number of interchangeable surgical tool end effectors each having a uniform connector portion for interchangeable engagement with the end effector connecting assembly of the surgical instrument.

12 Claims, 16 Drawing Sheets

U.S. PATENT DOCUMENTS

| | | |
|---|---|---|
| 1,839,726 | 1/1932 | Arnold . |
| 1,919,120 | 7/1933 | Oconnor . |
| 1,963,173 | 6/1934 | Morin . |
| 2,053,868 | 9/1936 | Grosso . |
| 2,384,304 | 9/1945 | Helfrick . |
| 2,473,266 | 6/1949 | Wexler . |
| 2,594,086 | 4/1952 | Smith . |
| 2,623,517 | 12/1952 | Barlow . |
| 2,701,562 | 2/1955 | Michael et al. . |
| 3,070,088 | 12/1962 | Brahos . |
| 3,129,706 | 4/1964 | Reynolds, Jr. . |
| 3,168,093 | 2/1965 | Gauthier . |
| 3,384,077 | 5/1968 | Gauthier . |
| 3,463,144 | 8/1969 | Hammond . |
| 3,509,873 | 5/1970 | Karlin et al. . |
| 3,522,799 | 8/1970 | Gauthier . |
| 3,680,546 | 8/1972 | Asrican . |
| 3,724,449 | 4/1973 | Gauthier . |
| 3,747,592 | 7/1973 | Santos . |
| 3,749,088 | 7/1973 | Gauthier . |
| 3,858,578 | 1/1975 | Milo . |
| 3,965,890 | 6/1976 | Gauthier . |
| 3,998,217 | 12/1976 | Trumbull . |
| 4,010,741 * | 3/1977 | Gauthier ........................ 600/227 |
| 4,048,987 | 9/1977 | Hurson . |
| 4,165,746 | 8/1979 | Burgin . |
| 4,190,042 | 2/1980 | Sinnreich . |
| 4,254,763 | 3/1981 | McCready . |
| 4,337,762 | 7/1982 | Gauthier . |
| 4,421,107 | 12/1983 | Estes . |
| 4,421,108 | 12/1983 | Cabrera . |
| 4,424,724 | 1/1984 | Bookwalter . |
| 4,430,991 | 2/1984 | Darnell . |
| 4,457,300 | 7/1984 | Budde . |
| 4,467,791 | 8/1984 | Cabrera . |
| 4,492,229 | 1/1985 | Grunwald . |
| 4,562,832 | 1/1986 | Wilder et al. . |
| 4,627,421 | 12/1986 | Symbas et al. . |
| 4,702,230 | 10/1987 | Pelta . |
| 4,726,356 | 2/1988 | Santilli et al. . |
| 4,744,363 | 5/1988 | Hasson . |
| 4,747,395 | 5/1988 | Brief . |
| 4,765,311 | 8/1988 | Kulik et al. . |
| 4,796,846 | 1/1989 | Meier et al. . |
| 4,813,401 | 3/1989 | Greishaber . |
| 4,829,985 | 5/1989 | Couetil . |
| 4,852,552 | 8/1989 | Chaux . |
| 4,865,019 | 9/1989 | Phillips . |
| 4,932,395 | 6/1990 | Mehdizadeh . |
| 4,949,707 | 8/1990 | Levahn et al. . |
| 5,000,163 | 3/1991 | Ray et al. . |
| 5,025,779 | 6/1991 | Bugge . |
| 5,052,373 | 10/1991 | Michelson . |
| 5,052,374 | 10/1991 | Alverez-Jacinto . |
| 5,067,477 | 11/1991 | Santangelo . |
| 5,088,472 | 2/1992 | Fakhrai . |
| 5,167,223 | 12/1992 | Koros et al. . |
| 5,231,974 | 8/1993 | Giglio et al. . |
| 5,284,130 | 2/1994 | Ratliff . |
| 5,299,563 | 4/1994 | Seton . |
| 5,306,234 | 4/1994 | Johnson . |
| 5,375,481 | 12/1994 | Cabrera et al. . |
| 5,400,774 | 3/1995 | Villalta et al. . |
| 5,503,617 | 4/1996 | Jako . |
| 5,514,077 | 5/1996 | Rabban . |
| 5,520,610 | 5/1996 | Giglio et al. . |
| 5,727,569 | 3/1998 | Benetti et al. . |
| 5,730,757 | 3/1998 | Benneti et al. . |
| 5,749,892 | 5/1998 | Vierra et al. . |
| 5,755,660 | 5/1998 | Tyagi . |
| 5,782,753 | 7/1998 | Defonzo et al. . |
| 5,807,243 | 9/1998 | Vierra et al. . |
| 5,857,965 | 1/1999 | Rootman et al. . |
| 5,899,425 * | 5/1999 | Corey, Jr. et al. ................ 600/229 |
| 5,947,896 * | 9/1999 | Sherts et al. ........................ 600/229 |
| 5,976,080 * | 11/1999 | Farascioni ........................ 600/213 |
| 6,007,486 | 12/1999 | Hunt et al. . |
| 6,030,340 * | 2/2000 | Maffei et al. ........................ 600/233 |
| 6,102,853 * | 8/2000 | Scirica et al. ........................ 600/227 |

\* cited by examiner

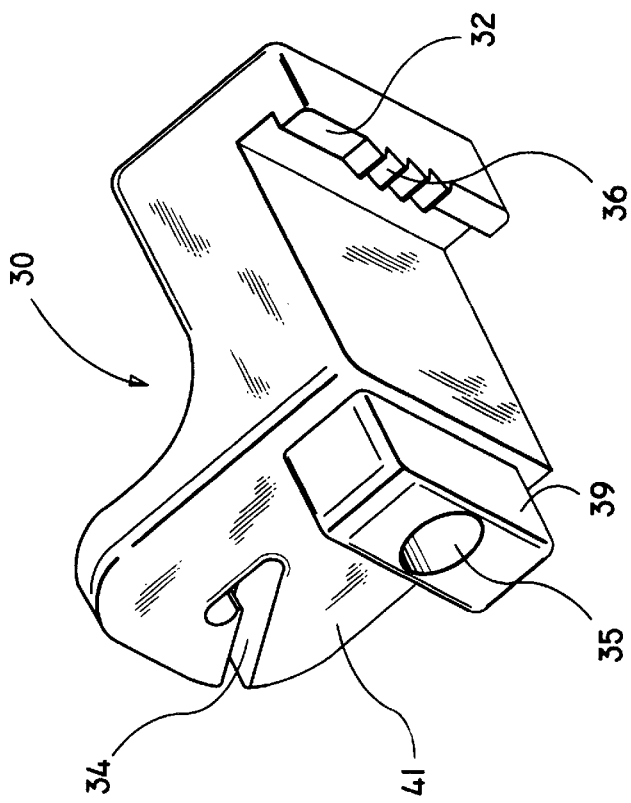
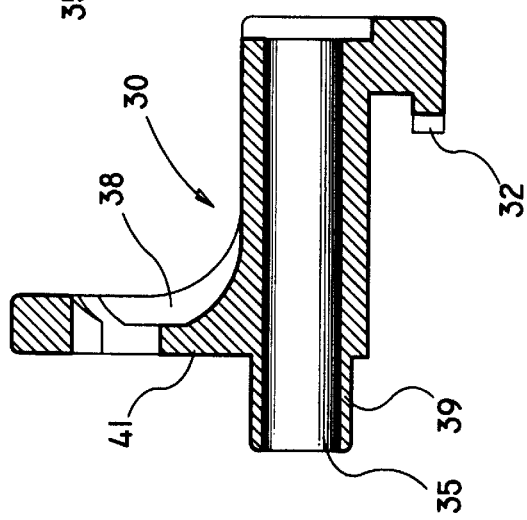
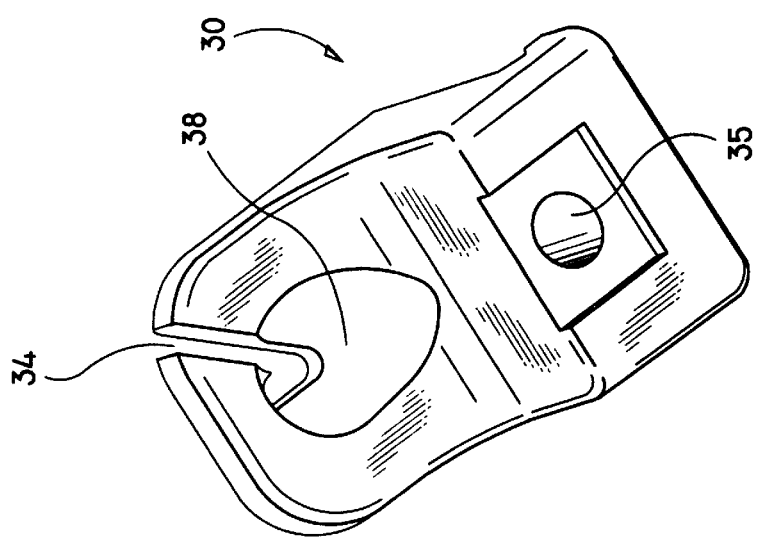
FIG. 6B
FIG. 6C
FIG. 6A

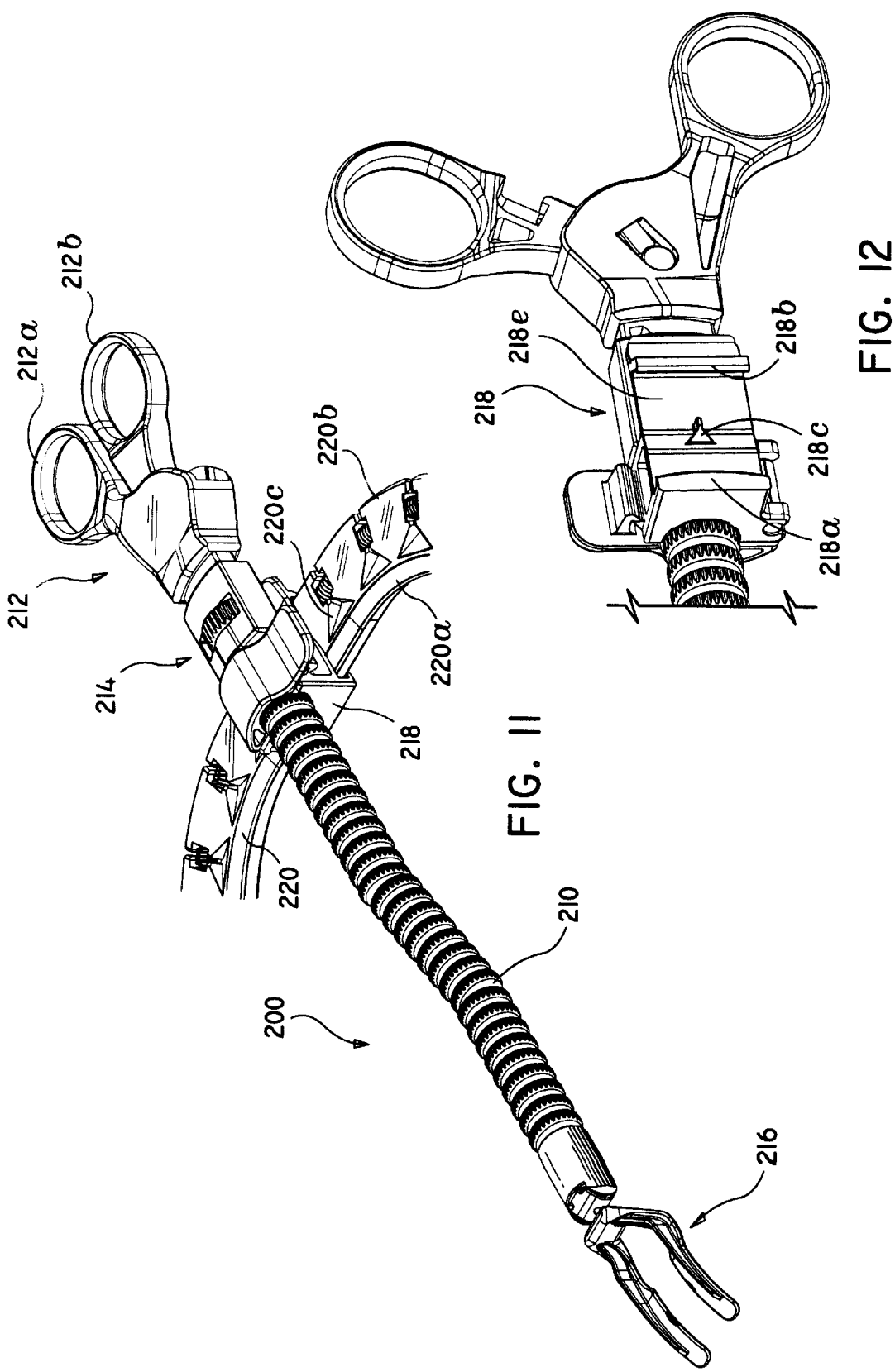

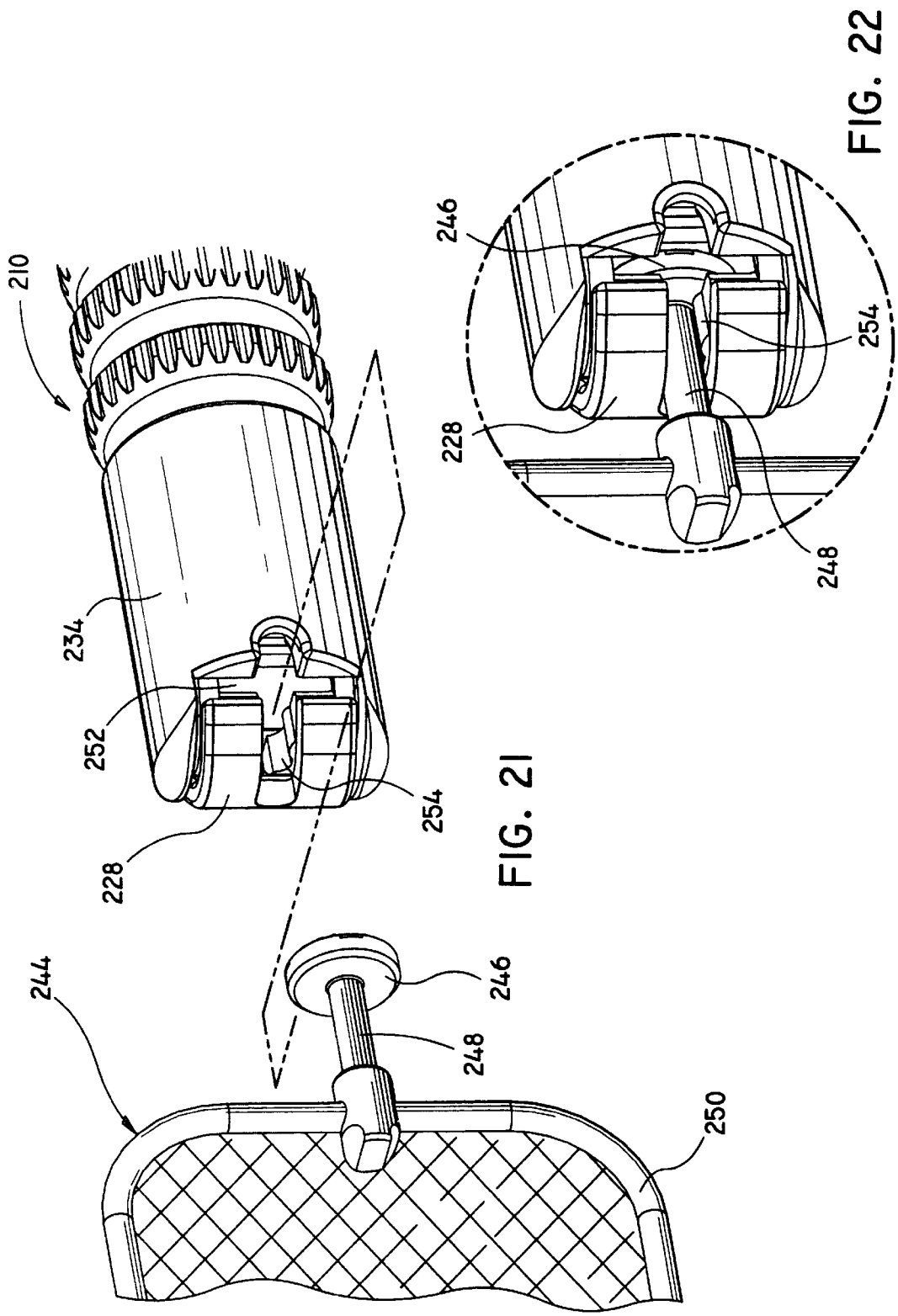

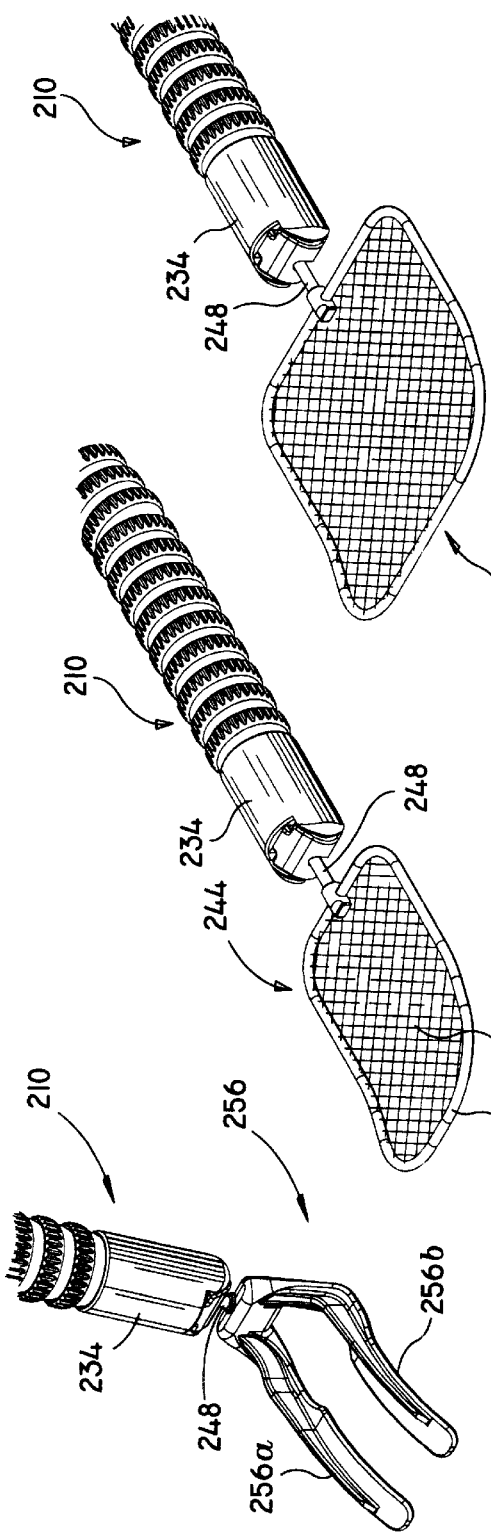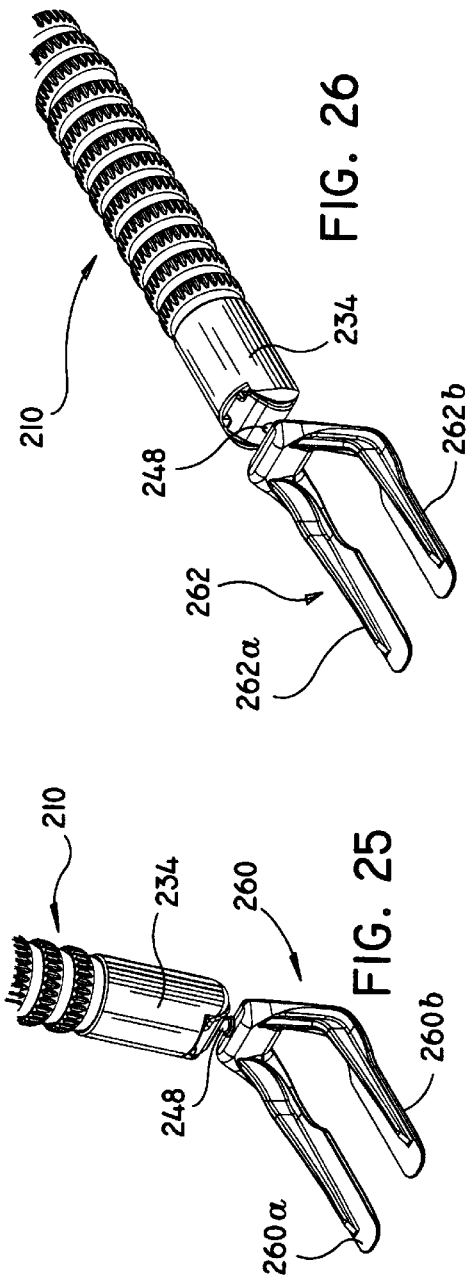

SURGICAL INSTRUMENT

CROSS REFERENCE TO RELATED APPLICATIONS

This application is a division of U.S. patent application Ser. No. 09/236,311 filed Jan. 22, 1999, U.S. Pat. No. 6,102,853 which claims priority to U.S. Provisional Application Ser. No. 60/072,405 filed Jan. 23, 1998 and to U.S. Provisional Application Ser. No. 60/105,364 filed Oct. 23, 1998. The contents of each of these applications are hereby incorporated by reference in their entirety.

BACKGROUND

1. Technical Field

The subject disclosure relates to minimally invasive surgical procedures and apparatus, and more particularly to surgical instrumentation for performing surgery associated with the thoracic cavity.

2. Background of Related Art

It is well established that the performance of various types of surgical procedures using less invasive techniques and instrumentation has provided numerous physical benefits to the patient while reducing the overall cost of such procedures. One area, for example, which has experienced a great increase in the performance of less invasive procedures is in the area of heart surgery. In particular, coronary artery bypass graft (CABG) procedures have been performed using less invasive techniques with much success.

Access to the patient's thoracic cavity for such procedures in the past was typically achieved by a large longitudinal incision in the chest. This procedure, referred to as a median sternotomy, requires a saw or other cutting instrument to cut the sternum and allow two opposing halves of the rib cages to be spread apart. U.S. Pat. No. 5,025,779 to Bugge discloses a retractor which is designed to grip opposite sternum halves and spread the thoracic cavity apart. The large opening which is created by this technique enables the surgeon to directly visualize the surgical site and perform procedures on the affected organs. However, such procedures that involve large incisions and substantial displacement of the rib cage are often traumatic to the patient with significant attendant risks. The recovery period may be extended and is often painful. Furthermore, patients for whom coronary surgery is indicated may need to forego such surgery due to the risks involved with gaining access to the heart.

U.S. Pat. No. 5,503,617 to Jako discloses a retractor configured to be held by the surgeon for use in vascular or cardiac surgery to retract and hold ribs apart to allow access to the heart or a lung through an operating window. The retractor includes a rigid frame and a translation frame slidably connected to the rigid frame. Lower and upper blades are rotatably mounted to the rigid frame and the translation frame respectively. Such a "window" approach requires instrumentation that can be inserted into and manipulated within the limited space available in and around the surgical site.

Therefore, a continuing need exists for more versatile and varied surgical instrumentation which facilitates performing surgical procedures in limited access cavities of a patient during less invasive surgical procedures.

SUMMARY

The present disclosure addresses the above-noted needs while providing surgical instrumentation that has many unique features and advantages over the prior instrumentation. The presently disclosed surgical instrumentation provides greater versatility during surgical procedures which are less invasive than traditional procedures.

For example, in one embodiment, the present disclosure provides a mounting assembly for mounting a surgical instrument to a base, wherein a clip portion and a cover portion function together to to retain the shaft of a surgical instrument therein and thereby fix the length of the instrument shaft relative to the base and an operative site. This is particularly advantageous in that during surgical procedures where free space in and around the surgical site is at a minimum, the presently disclosed mounting assembly facilitates positioning a surgical instrument relative to the surgical site so that only the minimum portion of the instrument is positioned in the sparse free space.

In an alternative embodiment, a mounting assembly for mounting a surgical instrument to a base is provided which includes first and second opposed mounting sections. The mounting assembly includes an instrument retaining area configured and dimensioned to removably retain the shaft of a surgical instrument therein.

In another aspect of the present disclosure, a surgical instrument is provided which includes a handle, a tool member, and an articulating arm which operatively connects the handle and the tool member. The articulating arm includes a number of arm segments and a number of reinforcing segments each of the various segments having a concave surface and a convex surface. The reinforcing segments have a maximum width which is less than a maximum width of the arm segments. In a particularly advantageous feature, the arm segments and reinforcing segments are arranged in a nested series to define a flexible column, wherein a cable extends from the handle through the a passageway in the segments to the distal end of the articulating arm.

In one aspect of the above embodiment, the reinforcing segments each includes a number of protrusions to facilitate making contact with the inner surface of the adjacent arm segment. In another aspect, each of the protrusions forms a tapered end.

In another embodiment, the present disclosure provides a surgical instrument including a handle having first and second relatively movable handle portions, a tool member, an articulating arm which operatively connects the handle and the tool member. The articulating arm includes a plurality of arm segments arranged in a series to form a flexible column. A cable is provided which extends from the handle through the passageway to the distal end of the articulating arm such that relative movement of the first and second handle portions to a first predetermined configuration causes the cable to be tensioned a predetermined amount. Finally, a tension adjustment mechanism is provided which includes an actuator and a slide housing operatively associated with the handle, such that upon movement of the actuator within a finite predetermined range of motion, the tension imparted in the cable may be incrementally adjusted and maintained at any magnitude associated with the predetermined range of motion of the actuator.

In yet another aspect of the present disclosure, a surgical instrument is provided which includes a handle having first and second relatively movable portions, and an articulating arm extending from the handle. The articulating arm includes a number of arm segments arranged in a series to form a flexible column, each of the arm segments defining an aperture therethrough such that a passageway is formed from a proximal end of the articulating arm to a distal end of the articulating arm. A cable is provided which extends from the handle through the passageway to the distal end of the articulating arm such that relative movement of the first and second handle portions to a first predetermined configuration causes the cable to be tensioned a predetermined amount. Finally, the present embodiment includes an end effector connecting assembly disposed at the distal end portion of the articulating arm. The end effector connecting assembly includes a housing, and a coupling member operatively connected to the distal end of the cable and movable relative to the housing from a closed position to an open position. The coupling member is operative to facilitate the removal or attachment of and end effector from the distal end of the articulating arm.

The present disclosure also provides the user with a uniquely advantageous surgical instrumentation kit including a surgical instrument having a handle, an articulating arm which forms a flexible column, and an end effector connecting assembly disposed at the distal end portion of the articulating arm. The coupling member is capable of retaining a connection portion of an end effector and when disposed in the open position. Preferably, the coupling member facilitates the removal or attachment of and end effector from the distal end of the articulating arm. The surgical instrumentation kit includes a number of interchangeable surgical tool end effectors each having a uniform connector portion for interchangeable engagement with the end effector connecting assembly of the surgical instrument. Finally, the surgical instrumentation kit includes a mounting assembly for mounting the surgical instrument to a base.

BRIEF DESCRIPTION OF THE DRAWINGS

Various preferred embodiments are described herein with reference to the drawings, wherein:

FIG. 6A is a rear perspective view showing the second mounting section of the instrument holder;

FIG. 6B is a perspective view showing the opposite side of the second mounting section of FIG. 6A.

FIG. 6C is a cross-sectional view of the second mounting section;

FIG. 11 is a perspective view of an alternative embodiment of a surgical instrument in accordance with the present disclosure;

FIG. 12 is a partial perspective view of the underside of a mounting assembly for the embodiment of FIG. 11;

FIG. 21 is a partial perspective view illustrating an end effector mounting structure;

FIG. 22 is an enlarged partial perspective view of a connection between an end effector and a distal end portion of the surgical instrument;

FIG. 23 is a partial perspective view of a distal end of a heart stabilizer end effector connected to the surgical instrument;

FIG. 25 is a partial perspective view illustrating an alternative embodiment of a heart stabilizing end effector connected to the surgical instrument;

FIG. 26 is a partial perspective view illustrating a further alternative heart stabilizing end effector attached to the surgical instrument;

FIG. 27 is a partial perspective view illustrating a tissue manipulating end effector connected to the distal end of the surgical instrument;

FIG. 28 is a partial perspective view showing an alternative tissue manipulating end effector connected to the distal end of the surgical instrument.

DETAILED DESCRIPTION OF PREFERRED EMBODIMENTS

The present disclosure is directed to various embodiments of a surgical instrument and assemblies for mounting the surgical instrument to a fixed base such that the length of a shaft of the instrument may be varied relative to the base. Initially, an embodiment of an instrument mounting assembly (holder) will be described with reference to FIGS. 1–12, and will refer to surgical instruments described in a copending application. Thereafter, embodiments of an alternative surgical instrument and mounting assembly will be described with reference to FIGS. 13–31. It is contemplated that the various described mounting assemblies may be used with the various described surgical instruments herein.

Figure 1:
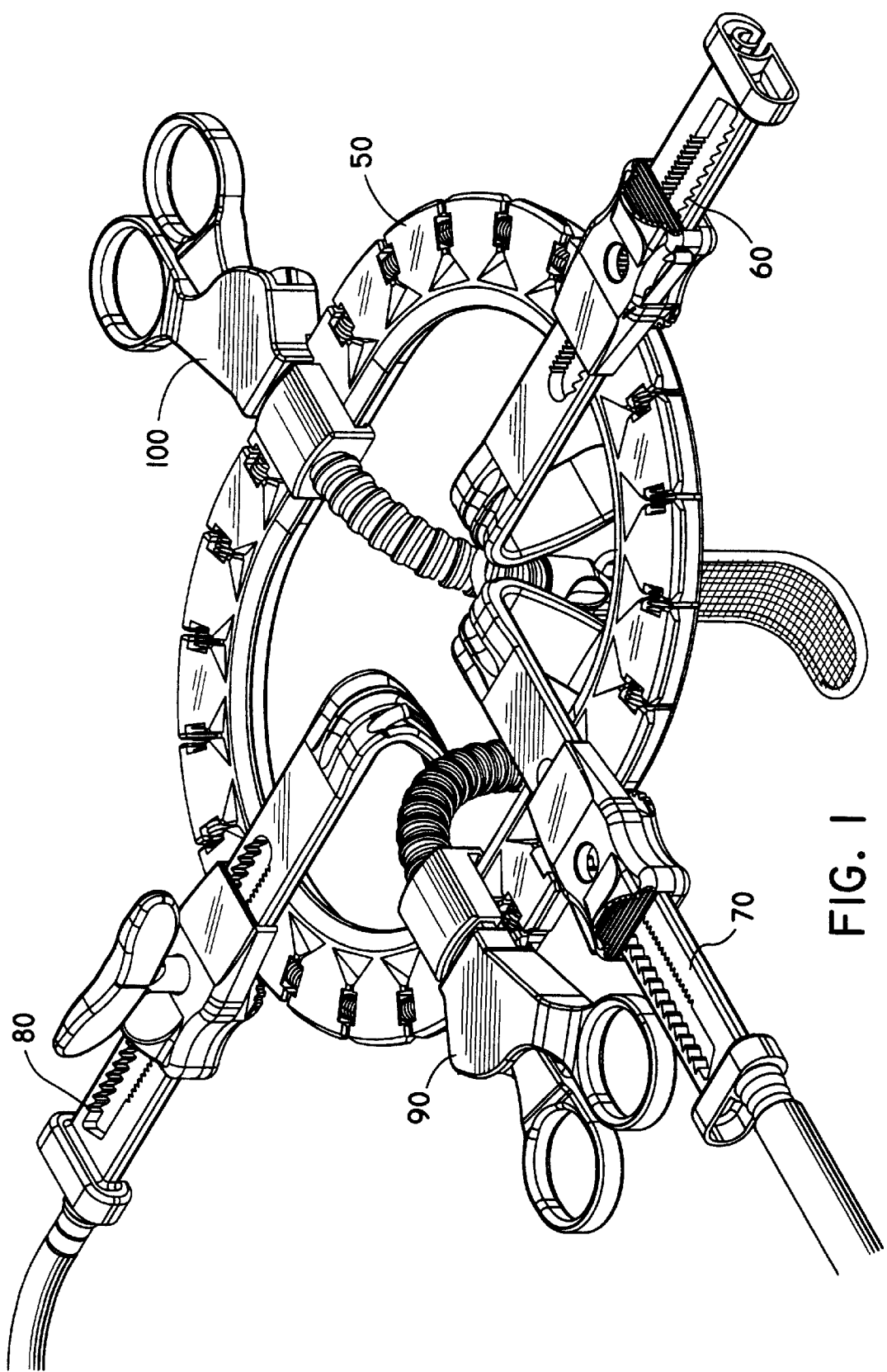
FIG. 1 is a perspective view of a first embodiment of a surgical retraction system incorporating a variety of retractors, a heart manipulator and a heart stabilizer, all positioned on a base.
Figure 2:
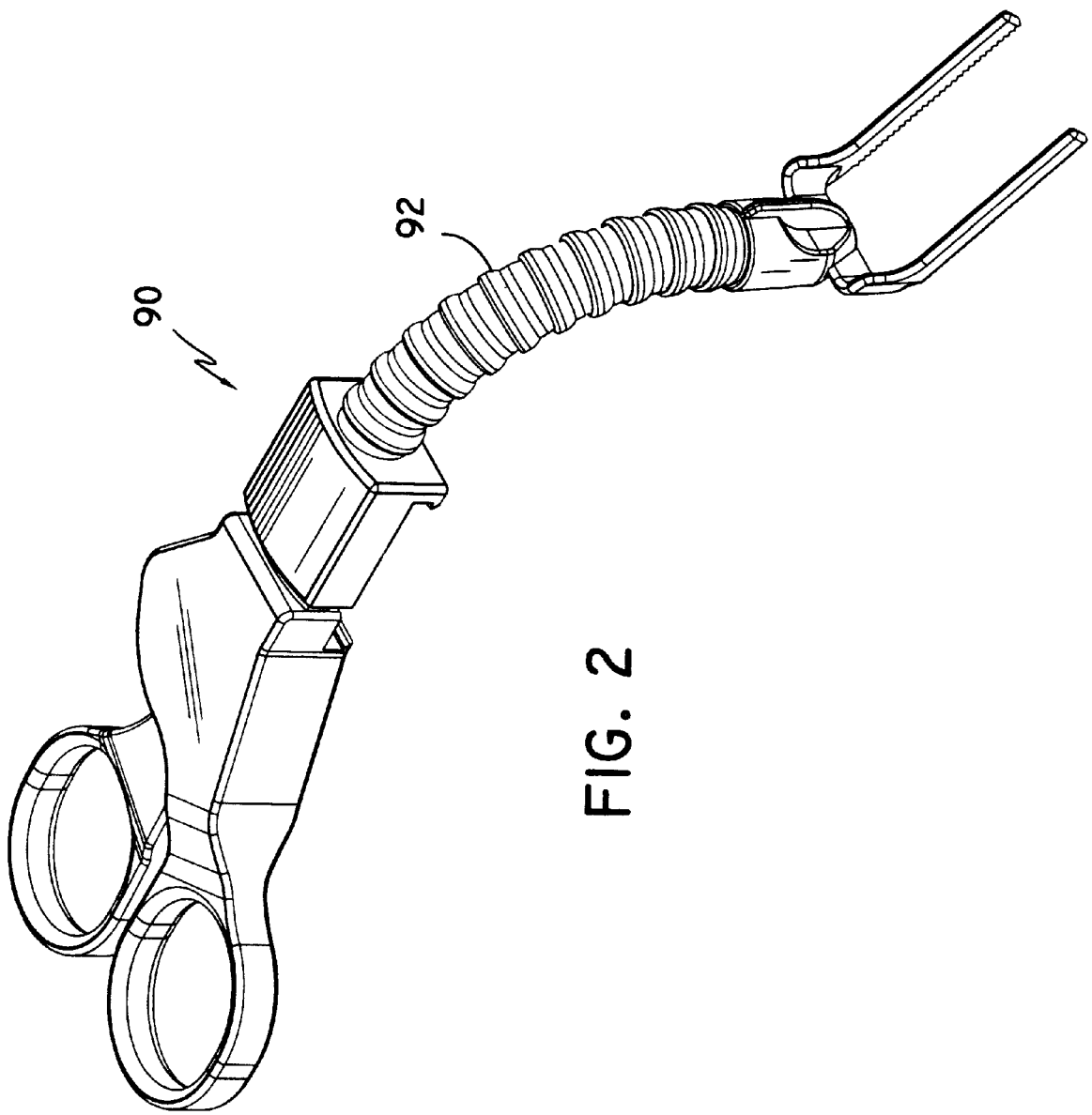
FIG. 2 is a perspective view the heart stabilizer of FIG. 1.

Referring to FIGS. 1–12, the instrument mount (holder) embodiment illustrated therein is designed to enable adjustment of the length of the articulating arm of an instrument such as the heart stabilizer and heart manipulator disclosed in U.S. patent application Ser. No. 08/718,283, filed Sep. 20, 1996, the contents of which are incorporated herein by reference in their entirety. FIG. 1 is a drawing from the '283 patent application and shows base 50, retractors 60, 70 and 80, heart stabilizer 90, and heart manipulator 100. A detailed description of these instruments, how they are mounted to the base 50, and their surgical function is disclosed in the '283 application. FIG. 2 is also a drawing from the '283 application and is included herein for convenience to show a heart stabilizer with an articulating arm 92.

Figure 3:
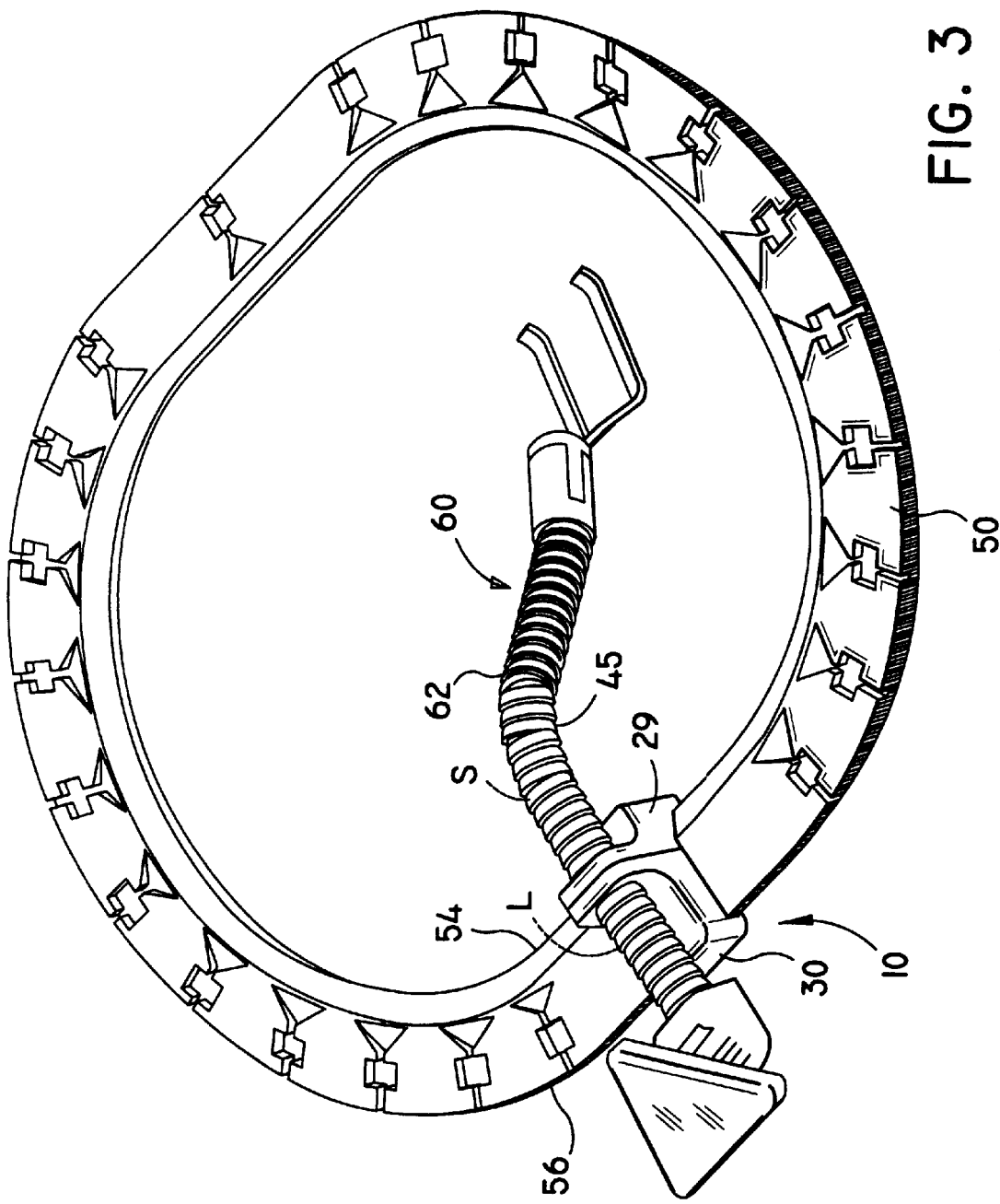
FIG. 3 is a perspective view showing the instrument mount (holder) of the present disclosure positioned on a base and supporting a heart stabilizer.
Figure 4:
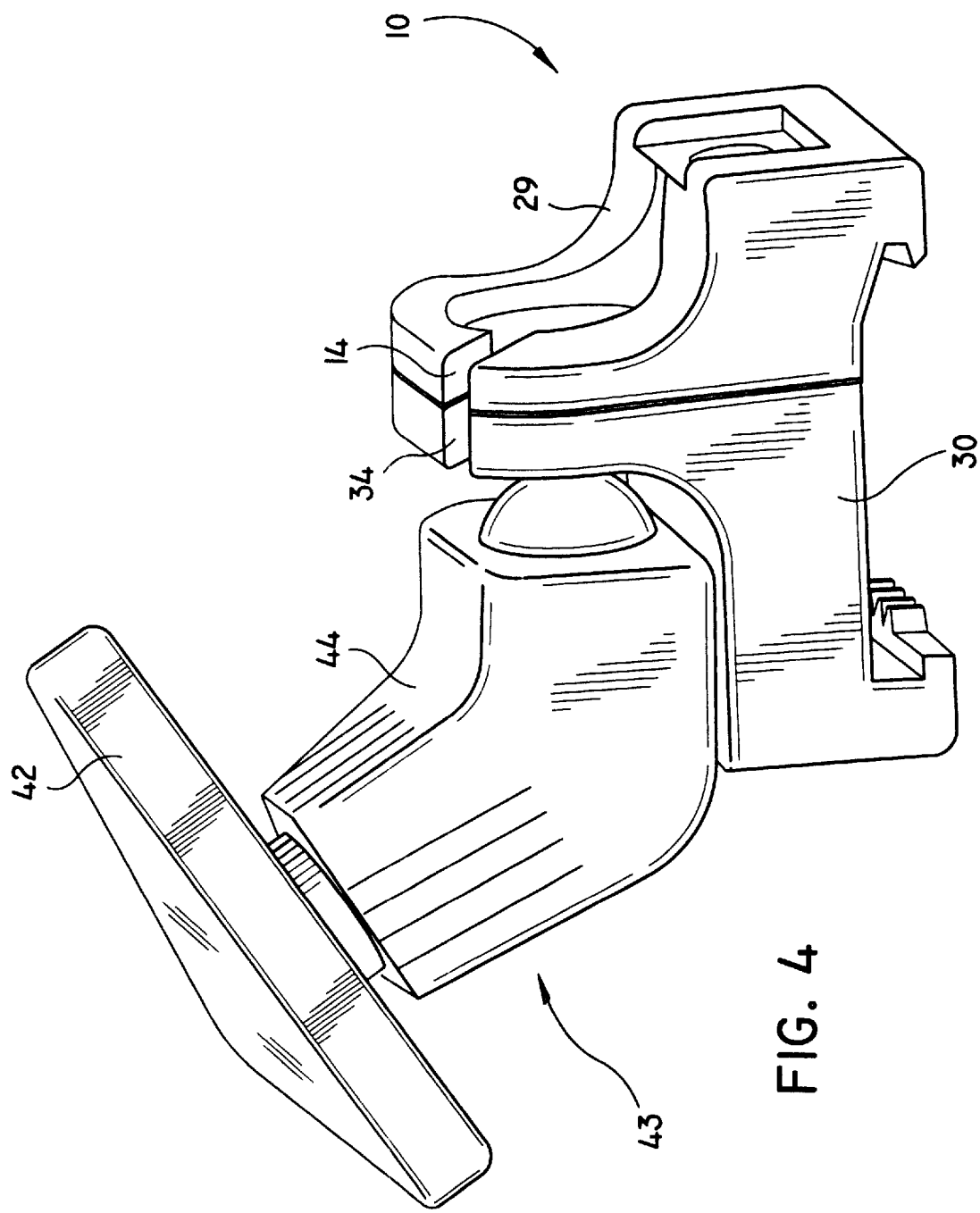
FIG. 4 is a perspective view showing the instrument holder and the cable locking mechanism, with the integral cable removed for clarity.
Figure 5A:
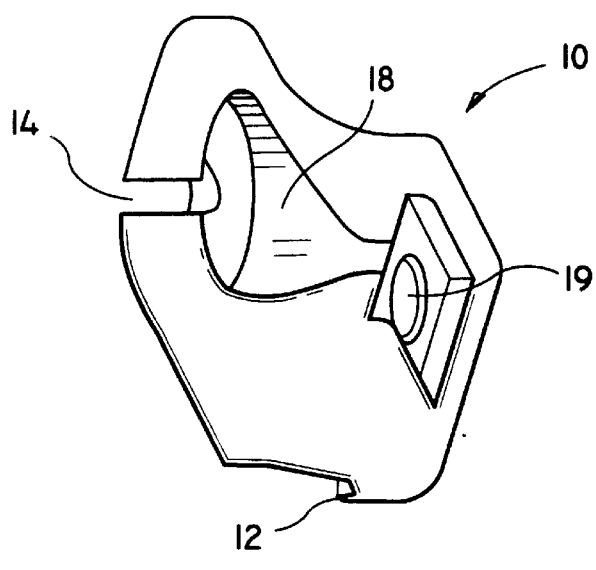
FIG. 5A is a top perspective view illustrating a first mounting section of the instrument holder.
Figure 5B:
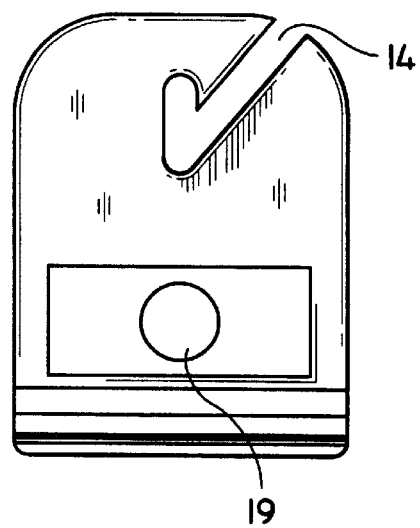
FIGS. 5B and 5C are rear and rear perspective views, respectively, of the first mounting section of FIG. 5A.
Figure 5C:
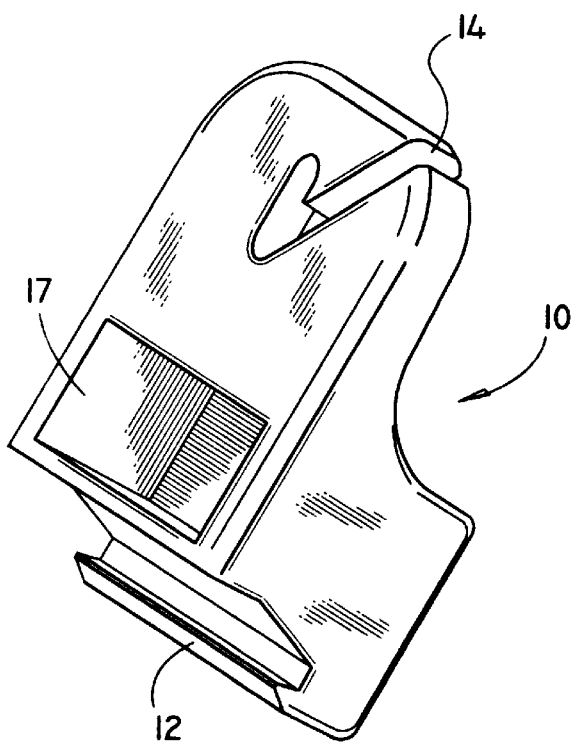
Figure 5D:
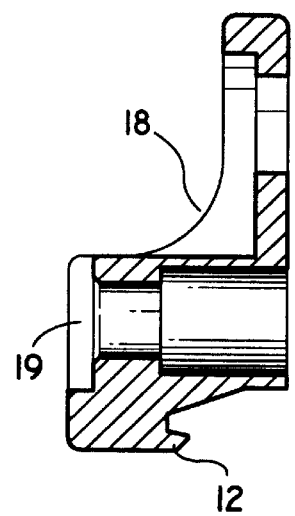
FIG. 5D is a cross-sectional view of the first mounting section.

Referring to FIGS. 3 and 4, the present disclosure in a first embodiment, includes an instrument holder 10 comprising first and second mounting sections 29 and 30, respectively which are fitted together by a groove and tongue arrangement. Mounting section 29 includes a lip 12 which is hooked around the front edge 54 of base 50 as shown in FIG. 3. A recess 18, best shown in FIG. 5, is configured to receive the domes of an articulating arm 62 of heart stabilizer 90. Referring to FIGS. 5A–5D, articulating arm 62 is positioned in the first mounting section 29 by sliding a cable 47 (FIG. 12) through slot 14 formed in the top of first mounting section 29. Groove 17 is configured to mount tongue 39 of second mounting section 30 in the manner described below. Bore 19 receives a spring (not shown) which is secured to both mounting sections 29 and 30 to help retain first and second mounting sections 29 and 30 together while allowing them to be pulled slightly away from each other, against the force of the spring, to facilitate mounting to and release from base 50.

With reference to FIGS. 6A–6C, second mounting section 30 has a bottom lip 32 with a series of teeth 36 configured to mount to outer edge 56 of base 50 (FIG. 3). A tongue 39 protrudes outwardly from surface 41 to fit within groove 17 of first mounting section 29. Slot 34, similar to slot 14 of first mounting section 29, is configured to receive cable 47 of articulating arm 62 with adjacent domes seated within respective recesses 18 and 38. Opening 35 is for receiving the biasing spring described above.

Figure 7:
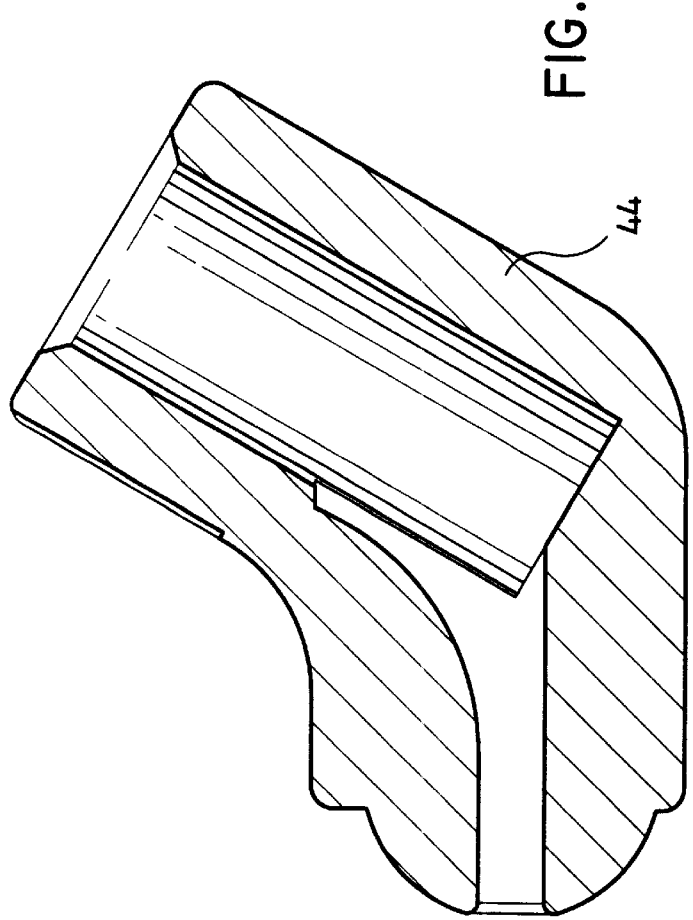
FIG. 7 is a cross-sectional view of the screw thread housing of the cable locking mechanism.
Figure 8:
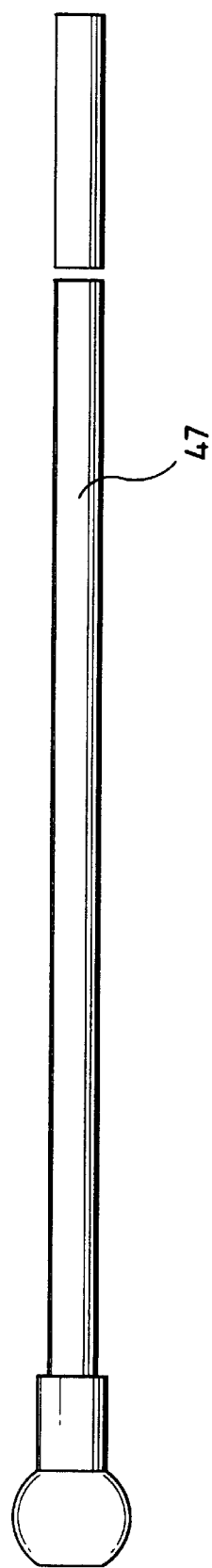
FIG. 8 illustrates a side view of the cable of the articulating arm.
Figure 10:
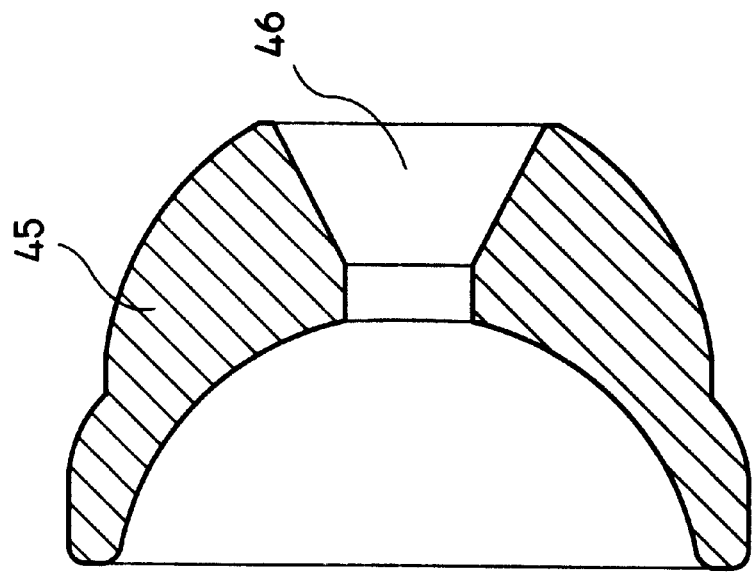
FIGS. 9 and 10 illustrate perspective and cross-sectional views, respectively, of one of the series of domes mounted on the cable to form an articulating arm.
Figure 9:
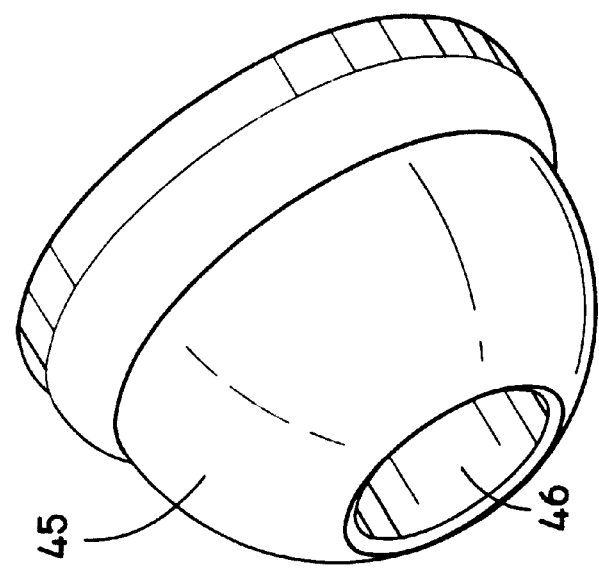

Rotation handle 42 of cable locking mechanism 43 of FIG. 4 is connected to a threaded rod which engages internal threads (not shown) of screw thread housing 44 (FIG. 7). The threaded rod is connected to the proximal end of cable 47 (FIG. 8). Upon rotation of handle 42, the threaded rod and connected cable 47 are moved out of housing 44 thereby pulling the cable to make articulating arm 62 taut which holds the heart stabilizer in position. For clarity, articulating arm 62 has been omitted from FIG. 4. Articulating arm 62 is formed by a plurality of domes 45, best shown in FIGS. 9 and 10, mounted on cable 47 (FIG. 8). An opening 46 is formed on each dome 45 to receive the cable therethrough.

It should be appreciated that while the above structure is described for use with a heart stabilizer it is also contemplated that a heart manipulator or any other instrument which includes the articulating arm 62 can be utilized. Various surgical procedures are also contemplated.

The use of the instrument holder will now be described in conjunction with a heart stabilizer for convenience. After the user decides where the stabilizer should be positioned, first and second mounting sections 29, 30 are pulled slightly apart to allow the lips 12 and 32 to engage the edges of the base 50. When released, the spring pulls first and second mounting sections 29 and 30 into abutment as shown in FIG. 3. The desired length of the stabilizer is identified and the appropriate portion of the cable 47 is placed through the slots 14 and 34 of first and second mounting sections 29 and 30. That is, if a shorter length stabilizer is desired, a more distal portion of articulating arm will be inserted through slots 14 and 13; if a larger length is desired, a more proximal portion will be inserted. Reference letter "L" and "S" in FIG. 3 provide by way of example, a sample location for a longer or shorter stabilizer, respectively, with respect to the position of FIG. 3. After articulating arm 62 is positioned in first and second mounting sections 29, 30, articulating arm 62 is maneuvered so the heart stabilizer is in the appropriate position. Rotation knob 42 is then rotated to retract the cable 47 to make articulating arm 62 rigid so as to maintain the stabilizer in the desired orientation relative to the heart tissue.

Referring now to FIGS. 11–29, an alternative embodiment of a surgical instrument generally designated as surgical instrument 200 will now be described in detail. Briefly, similar to the instrument embodiment described above, surgical instrument 200 includes a multi-configurable articulating arm 210 which is operable from a freely flexible condition to a rigid, locked configuration by way of a handle assembly 212. Surgical instrument 200 further includes a tension adjusting mechanism 214 to vary the degree of tension imparted in a cable of articulating arm 210. This enables the flexibility of the arm to be selectively adjusted. Surgical instrument 200 is further provided with one or more interchangeable end effectors or tools such as a heart stabilizer end effector 216 as shown in FIG. 11. The present disclosure also provides a mounting member, for example clamp 218, which provides for the secure and fixed attachment of surgical instrument 200 to a base 220.

Referring to FIGS. 11–15, clamp 218 as noted above, serves to removably attach surgical instrument 200 to base 220. Clamp 218 is secured to a base 220 by snapping lip portions 218a and 218b of a clip poriton 218e over inner and outer rim portions 220a and 220b of base member 220, respectively. A key portion 218c is formed on the underside of clamp 218 as shown in FIG. 12, and is configured and dimensioned to fit within keyways 220c formed around the periphery of base 220. In this manner, clamp 218 is prevented from sliding along base 220 thereby providing a secure rigid attachment of instrument 210 to base 220.

Figure 13:
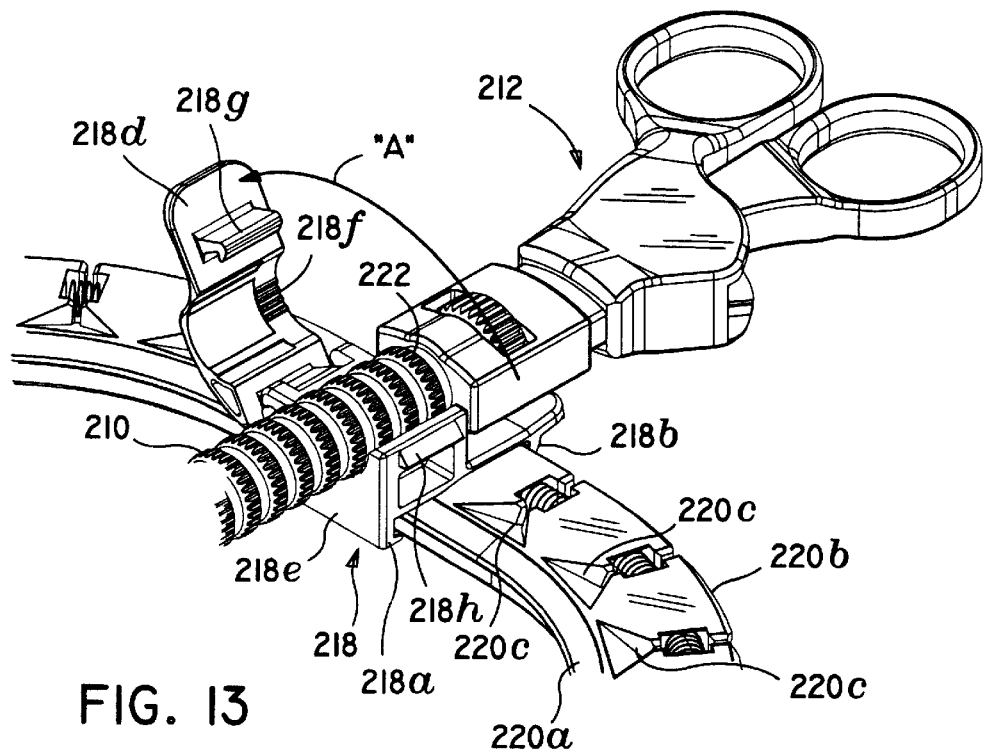
FIG. 13 is a partial perspective view illustrating operation of the mounting assembly.
Figure 14:
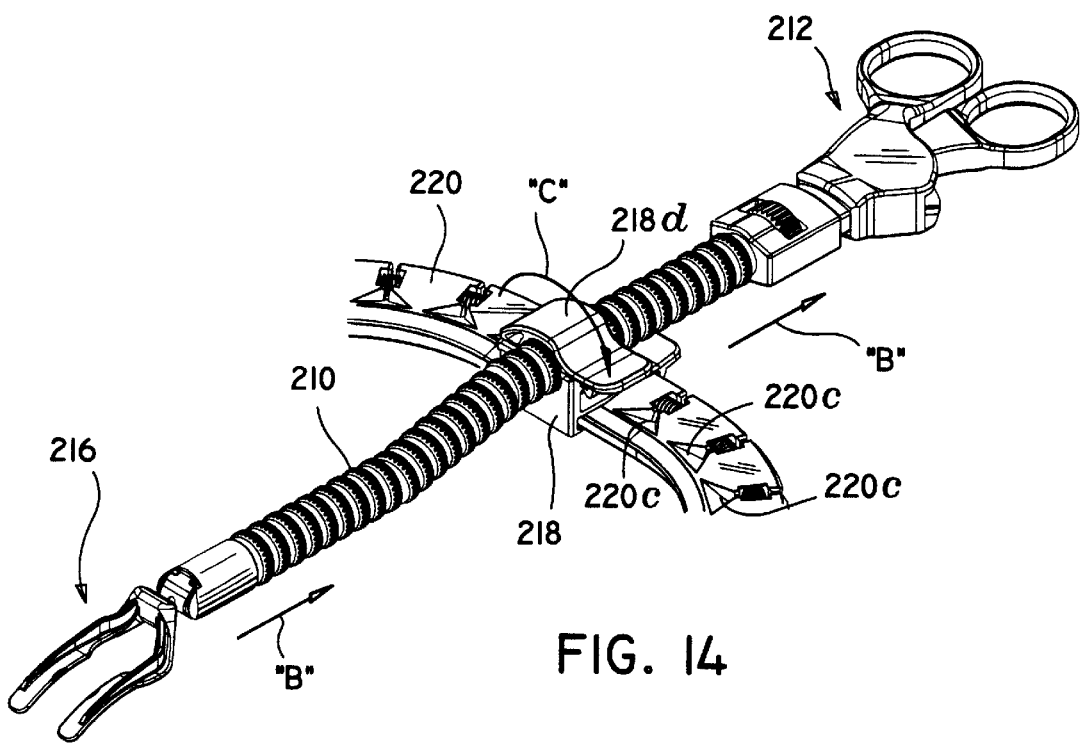
FIG. 14 is a partial perspective view illustrating the length adjusting characteristic of the mounting assembly.

Another particularly advantageous feature is illustrated in FIGS. 13 and 14 wherein the relative length of articulating arm 210 of instrument 200 may be lengthened or shortened with respect to base 220 by way of clamp 218. In particular, clamp 218 is provided with a pivotally mounted locking cover 218d. Clamp 218 is preferably molded to form an inner channel when closed to conform to the shape of articulating arm 210. To adjust the length of articulating arm 210 relative to base 220, locking cover 218d is pivoted open as indicated by arrow "A" in FIG. 13. Articulating arm 210 is moved to the desired length adjusted position, for example, proximally as indicated by arrow "B" in FIG. 14. "Length adjusted position" in this context refers to the length or amount of articulating arm 210 that is distal of the clamp and which extends through the opening of base 220 to the tissue site. Locking cover 218d is pivoted closed over the top of clip portion 218e so that knurled portions, such as teeth 218f formed on the inner surface of locking cover 218d, mesh with correspondingly shaped knurled portions or teeth 222 formed along periphery of the articulating arm segments. Locking cover 218d is secured in the locked position by the engagement of latch 218g with lock plate 218h.

Alternatively, articulating arm 210 may also be positioned in clamp 218 at any position along the length of articulating arm 210 and then mounting the assembled clamp and instrument to the base without having to subsequently reposition the instrument.

The structure and operation of the multi-configurable articulating arm 210 will now be described in detail with reference to FIGS. 15–20. Articulating arm 210 includes a series of elements 224 axially disposed about a flexible tensioning member such as cable 226 which is secured at a proximal end in movable tension control member 212b and at a distal end to end effector coupling 228. A coil spring 230 is also disposed on or around cable 226 between coupling 228 and a stepped through-bore 232 formed through coupling housing member 234 which is disposed about a bulbous distal end 236 of cable 226.

Figure 16:
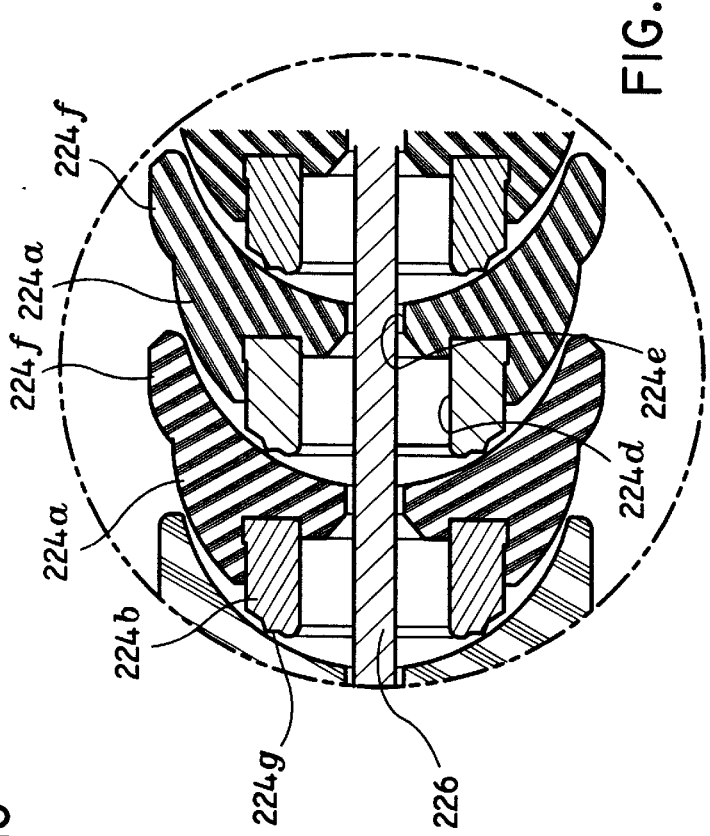
FIG. 16 is an enlarged view of the indicated area of detail shown in FIG. 15.
Figure 17:
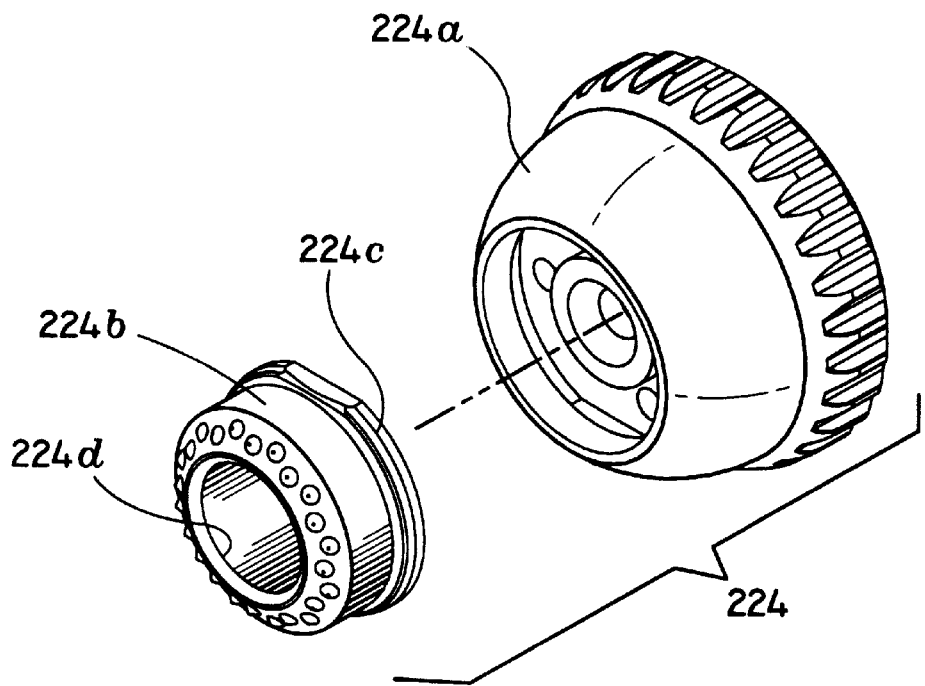
FIG. 17 is a perspective view with parts separated of one segment of an articulating arm of the present disclosure.
Figure 18:
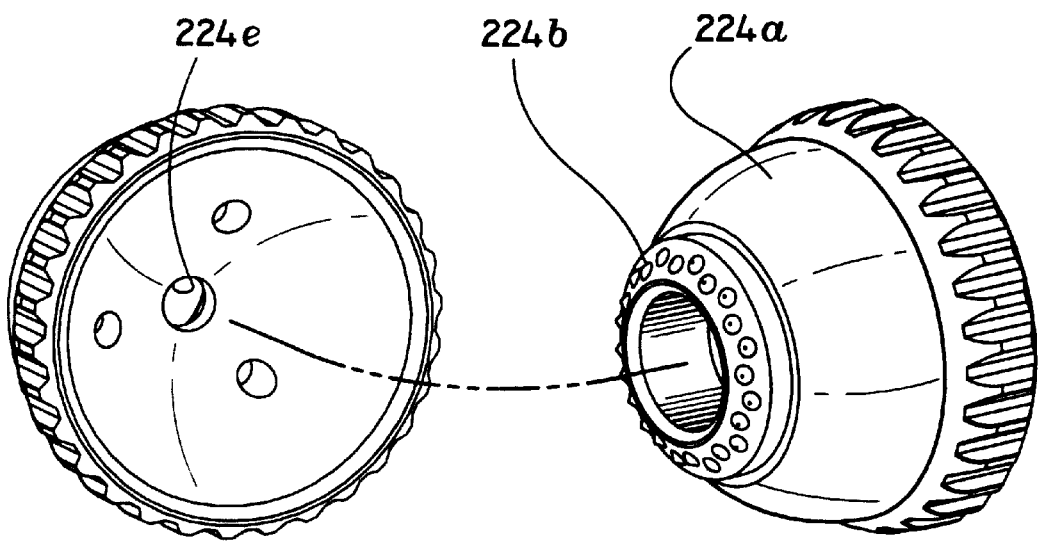
FIG. 18 is a perspective view with parts separated showing the relative positioning of two adjacent articulating arm segments.

Tension adjusting mechanism 214 includes housing portion 238 which includes a lateral slot formed therethrough to longitudinally retain a tension adjusting actuator member such as threaded dial 240, while permitting rotation thereof. Handle assembly 212 includes a distally extending threaded shaft portion 242 which is threadably received within dial 240 to facilitate selective proximal or distal selective movement of handle assembly 212 with respect to housing portion 238. Referring to FIGS. 16–18, each of articulating arm elements 224 include a dome shaped segment such as arm segment 224a and a reinforcing segment such as insert segment 224b snap fitted to the outer distal surface of arm segment 224a. Arm segments 224a are preferably formed of a polycarbonate material or the like while insert segments 224b are preferably formed of a metal material to provide reinforcing strength to enhance the rigidity of articulating arm 210 when in a tensioned condition. Arm segments 224a are preferably provided with molded recessed surfaces on a distal end thereof which correspond to and receive a proximal flange 224c of insert segments 224b. As best shown in FIG. 16, the internal diameter of inserts 224b as defined by inner surface 224d is much greater than the internal diameter defined by inner surface 224e of arm segments 224a. This construction facilitates flexion of articulating arm 210 so that cable 226 is guided in the general configuration of articulating arm 210 by arm segments 224a but permitted to swing through a greater arc prior to contacting inner surfaces 224d of inserts 224b. Furthermore, arm segments 224a are provided with shoulder portions 224f which serve to prevent significant gaps or pinch points from forming between adjacent articulating arm segments upon flexion thereof. Insert segments 224b are further provided with a series of conically shaped protrusions 224g which come to a point and serve as sharpened contact engagement points with the proximal surfaces of arm segments 224a upon tensioning of articulating arm 210.

Figure 19:
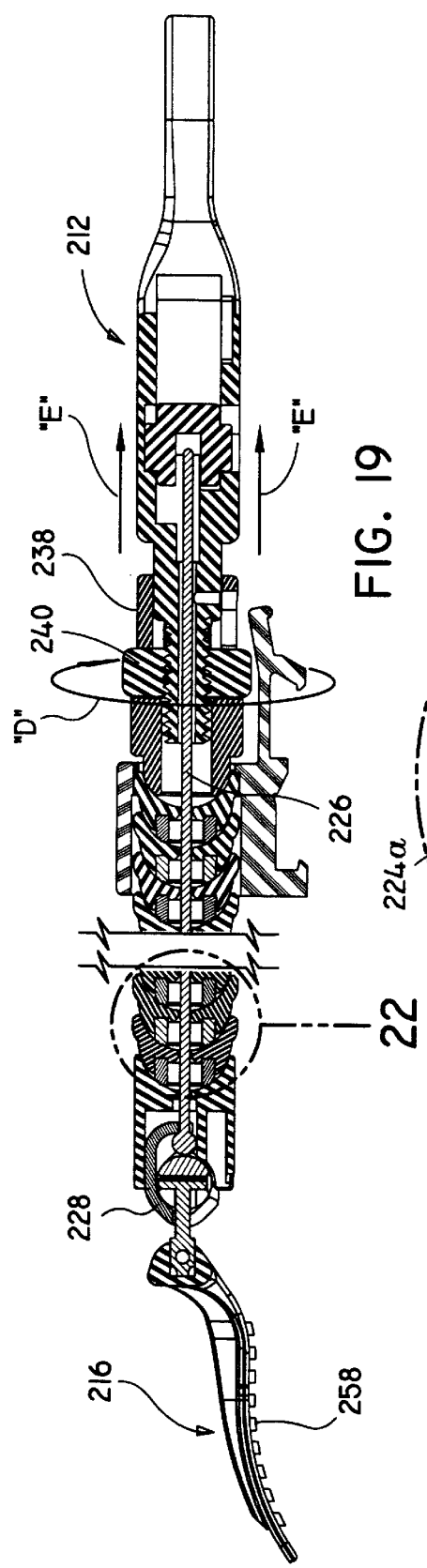
FIG. 19 is a horizontal cross-sectional view similar to FIG. 16, showing operation of the tension adjusting mechanism.
Figure 20:
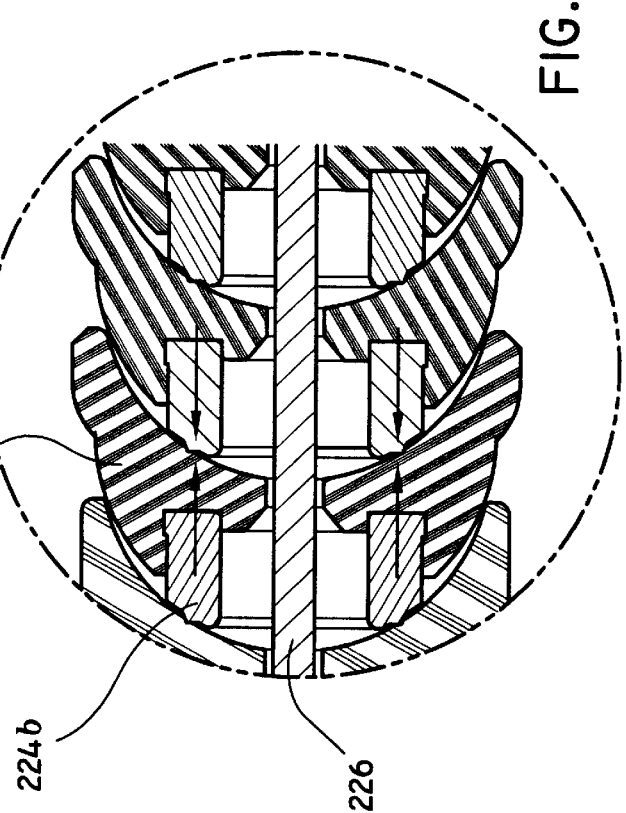
FIG. 20 is an enlarged view of the indicated area of detail of FIG. 19.

In operation, as shown in FIGS. 19 and 20, the tension adjusting mechanism may be adjusted to increase or decrease the amount of tension imparted to the cable 226 thereby adjusting the compression in the arm segments 224a and insert segments 224b and thus the rigidity of articulating arm 210 by way of adjusting dial 240. For example, dial 240 may be rotated in a clockwise fashion, as viewed from a proximal perspective indicated by arrow "D" in FIG. 19, to increase the amount of tension in cable 226 by moving handle assembly 212 proximally in the direction of arrows "E" with respect to housing section 238, thus providing a less flexible articulating arm 210. Conversely, dial 240 may be rotated in the opposite direction to decrease the amount of tension in cable 226, thus providing a more flexible articulating arm 210. Therefore, the flexibility of articulating arm 210 may be adjusted to suit the individual user's preference.

During a given surgical procedure, articulating arm 210 (which is either initially in a non-locked configuration or is placed in such configuration) is manipulated by the user to the desired configuration and/or position at the surgical site. To lock articulating arm 210 in the desired configuration, tension control lever 212b is squeezed toward stationary housing portion 212a. Cable 226 which is anchored in tension control lever 212b is thereby pulled proximally in the direction of arrows "E" of FIG. 19 such that insert segments 224b, which are axially aligned relative to each other, impinge into the inner surfaces of arm segments 224a to enhance the rigidity of articulating arm 210 and reduce the stresses created on arm segments 224a by reducing the moment arm length with respect to cable 226.

As illustrated in FIGS. 21–28, surgical instrument 200 includes an end effector connecting assembly formed at the distal end of articulating arm 210. An end effector, such as tissue manipulating attachment 244, is provided with a connector hub 246 disposed at a proximal end of a shaft portion 248 which is secured to the operative portion of the end effector such as stabilizer contact frame member 250. Hub portion 246 is received within a laterally directed opening 252 formed through distal end housing segment 234 and coupling member 228 as well as yoke 254 which is retained by coupling member 228 at the open distal end of housing section 234.

To attach a particular end effector to the distal end of articulating arm 210, tension control lever 212b is opened to its fully spaced-apart position away from stationary handle section 212a. Tension adjusting dial 240 is rotated to advance handle assembly 212 to its most closely approximated orientation with respect to slide housing 238 in order to enable spring 230 to bias coupling member 228 distally away from the open end of distal housing section 234. In this manner, a sufficient gap is formed between coupling 228 and the distal surface of housing 234 to permit the entry of hub 246 in lateral opening 252. Once the desired end effector is inserted in lateral opening 252, tension adjusting dial 240 is rotated to effect proximal movement of handle assembly 212 with respect to slide housing 238 in order to move coupling 228 proximally to secure the end effector within the distal end portion of articulating arm 210.

Various types of end effectors are contemplated for usage in connection with surgical instrument 200. Some examples of such end effectors are illustrated throughout FIGS. 23–28. For example, in the case of a procedure performed on the heart, heart stabilizing end effectors such as those shown in FIGS. 23–26 may be utilized in conjunction with instrument 200. In FIG. 23, heart stabilizer 256 is similar to heart stabilizer 216 (FIG. 15) except that mounting hub 246 is disposed away from end effector 256 at an angle significantly different from that of mounting hub 246 of end effector 216. Thus, when mounted upon instrument 200, heart stabilizer end effector 256 is oriented relative to the distal end of flexible arm 210 such that leg portions 256a and 256b extend at a much greater angle relative to a longitudinal axis of distal housing 234 than that of end effector 216. Although only two different angle settings are illustrated for the mounting of the working portions of the end effectors with respect to articulating arm 210, many different mounting angle may also be utilized, and are also contemplated by the present disclosure.

Figure 15:
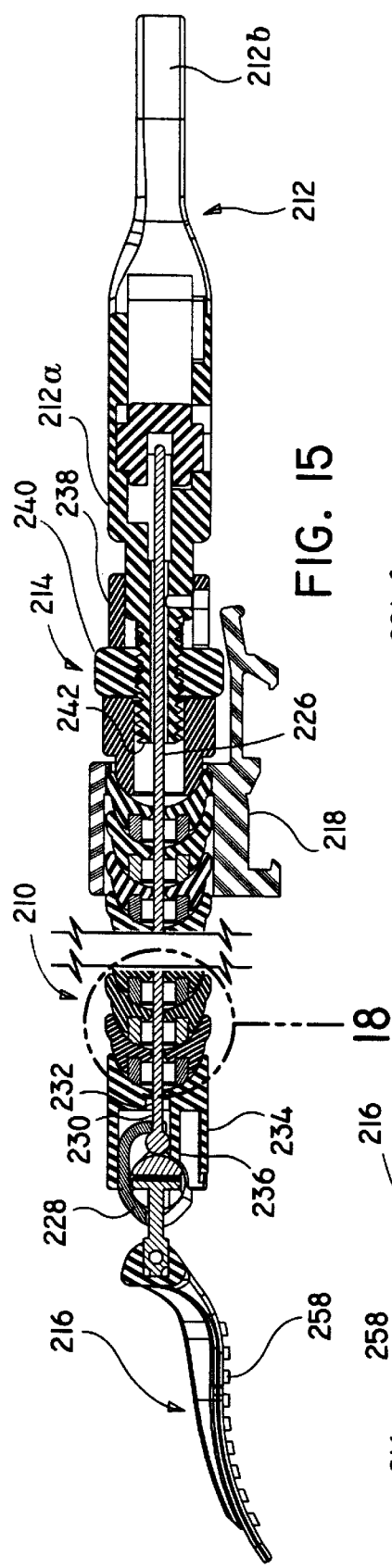
FIG. 15 is a horizontal cross-sectional view which illustrates a tensioning mechanism which forms a part of the surgical instrument.
Figure 24:
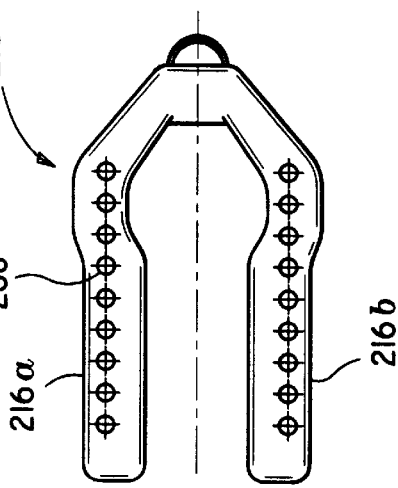
FIG. 24 is a view of a bottom surface of the heart stabilizer end effector of FIG. 23.

As shown in FIG. 24, it is contemplated that the various heart stabilizer end effectors may have protrusions extending from bottom surfaces of leg portions of the end effectors such as leg portions 216a and 216b so as to provide a gripping surface to better grip tissue contacted by the leg portions. Protruding portions 258 may be provided as circular flat extended protrusions as shown in FIGS. 15 and 24 or may have other suitable geometrical configurations to enhance gripping with the tissue surface.

FIG. 25 illustrates a further alternative heart stabilizer end effector 260 which is similar to heart stabilizer end effector 256 except that leg portions 260a and 260b are substantially planar in comparison with the arcuately flared leg portions 256a and 256b of heart stabilizer end effector 256. Similarly, FIG. 26 features heart stabilizer end effector 262 having substantially planar leg portions 262a and 262b in contrast to the arcuately flared leg portions 216a and 216b of heart stabilizer end effector 216 (FIG. 15).

Referring to FIG. 27, a tissue manipulating end effector 244 is shown attached to the distal end of articulating arm 210. Tissue manipulating end effector 244 includes a rigid peripheral frame member 264 and a flexible tissue contacting material such as mesh 266. Other surfaces or materials are contemplated for tissue manipulating end effector 244 such as solid materials of plastic, metal or the like. Referring to FIG. 28, an alternative embodiment of a tissue manipulating member is shown as tissue manipulating end effector 268 which includes a greater surface area over which to contact and manipulate tissue therewith.

Figure 29:
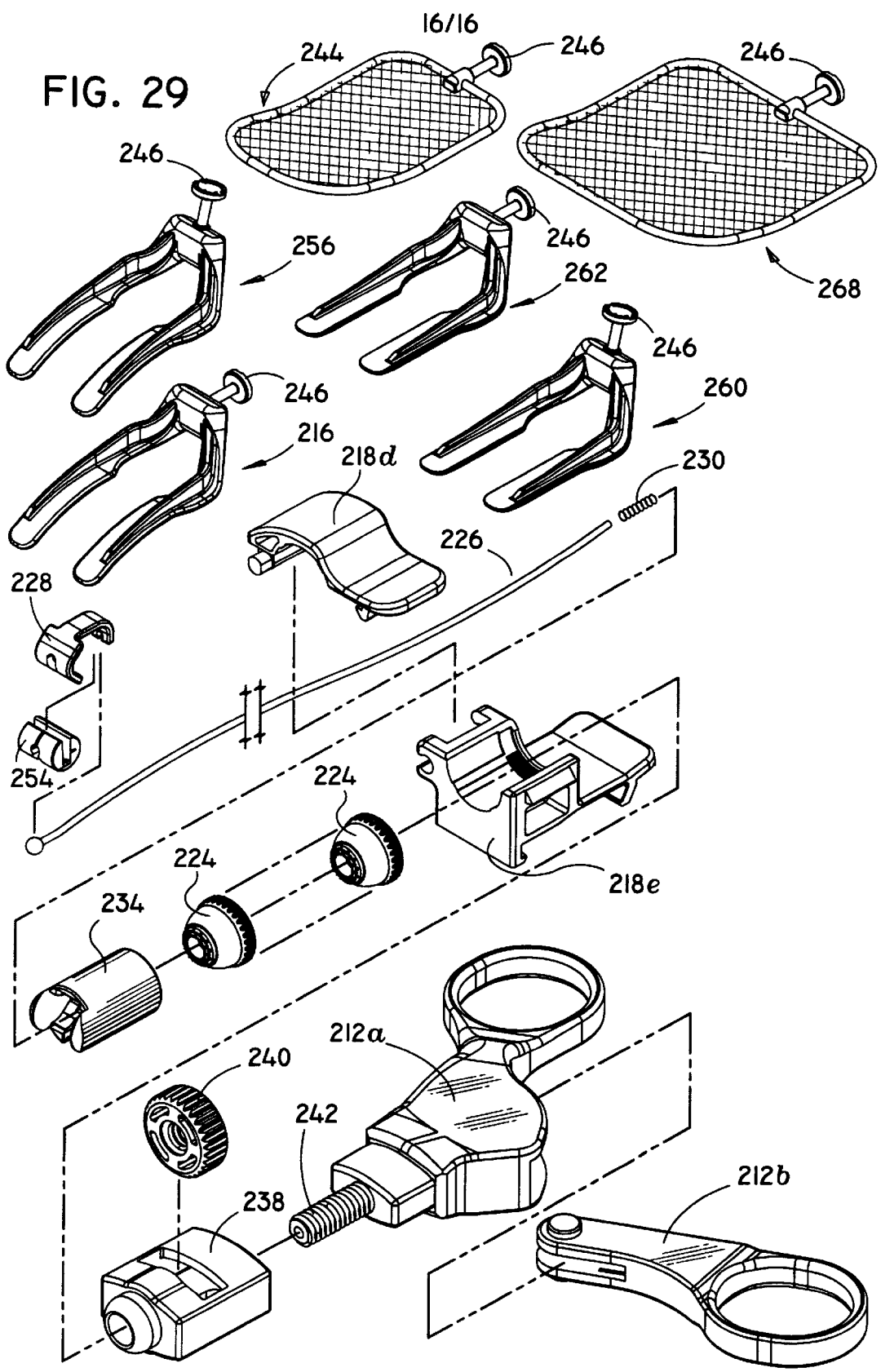
FIG. 29 is a view showing the contents of a kit including a plurality of end effectors and a surgical instrument shown with parts separated.

Referring to FIG. 29, one exemplary embodiment of an instrument kit is shown wherein the kit includes a surgical instrument 200 (shown with parts separated for illustrative components of the various structural members) and a number of different end effectors which will provide the surgeon with a greater selection and versatility throughout the surgical procedure. For example, a full range of heart stabilizing end effectors 216, 256, 262 and 260 having varying mounting orientations and leg configurations may be included. Additionally, differing tissue manipulating end effectors such as end effectors 244 and 268 may be included to also provide the user with a greater range of selection for a particular procedure.

It will be understood that various modifications may be made to the embodiments shown herein. Therefore, the above description should not be construed as limiting, but merely as exemplifications of preferred embodiments. Those skilled in the art will envision other modifications within the scope and spirit of the present disclosure.

What is claimed is:

1. A surgical instrument which comprises:
   a handle;
   a tool member; and
   an articulating arm which operatively connects the handle and the tool member, the articulating arm including:
     a plurality of arm segments each having a concave surface and a convex surface and each having a maximum width thereof;
     a plurality of reinforcing segments each having a concave surface and a convex surface, the plurality of reinforcing segments each having a maximum width thereof which is less than the maximum width of the plurality of arm segments, the plurality of arm segments and the plurality of reinforcing segments being arranged in a nested series to define a flexible column wherein each of the plurality of reinforcing segments is nested between adjacent ones of the plurality of arm segments, each of the plurality of arm segments and the plurality of reinforcing segments including an aperture formed therein so as to define a passageway which extends from a proximal portion of the articulating arm to a distal portion of the articulating arm; and
     a cable extending from the handle through the passageway to the distal end of the articulating arm.

2. A surgical instrument according to claim 1, wherein the reinforcing segments each includes a plurality of protrusions disposed thereon so as to facilitate making contact with the inner surface of the adjacent arm segment.

3. A surgical instrument according to claim 2, wherein each of the protrusions forms a tapered end.

4. A surgical instrument according to claim 1, wherein the plurality of reinforcing segments are metallic.

5. A surgical instrument which comprises:
   a handle having first and second relatively movable handle portions;
   a tool member;
   an articulating arm which operatively connects the handle and the tool member, the articulating arm including:
     a plurality of arm segments arranged in a series to form a flexible column, each of the arm segments defining an aperture therethrough such that a passageway is formed from a proximal end of the articulating arm to a distal end of the articulating arm;
     a cable extending from the handle through the passageway to the distal end of the articulating arm such that relative movement of the first and second handle portions to a first predetermined configuration causes the cable to be tensioned a predetermined amount; and
   a tension adjustment mechanism which includes an actuator and a slide housing operatively associated with the handle, such that upon movement of the actuator within a finite predetermined range of motion, the tension imparted in the cable may be incrementally adjusted and maintained at any magnitude associated with the predetermined range of motion of the actuator.

6. A surgical instrument according to claim 5, wherein the actuator is a dial which is threaded about a threaded shaft extending from the handle.

7. A surgical instrument which comprises:
   a handle which includes first and second relatively movable portions;
   an articulating arm extending from the handle, which includes:
     a plurality of arm segments arranged in a series to form a flexible column, each of the arm segments defining an aperture therethrough such that a passageway is formed from a proximal end of the articulating arm to a distal end of the articulating arm;
     a cable extending from the handle through the passageway to the distal end of the articulating arm such that relative movement of the first and second handle portions to a first predetermined configuration causes the cable to be tensioned a predetermined amount; and
   an end effector connecting assembly disposed at the distal end portion of the articulating arm, which includes:
     a housing; and
     a coupling member operatively connected to the distal end of the cable and movable relative to the housing from a closed position to an open position, the coupling member being configured and dimensioned such that when disposed the closed position, the coupling member is capable of retaining a connection portion of an end effector and when disposed in the open position, the coupling member permits the removal or attachment of and end effector from the distal end of the articulating arm.

8. A surgical instrument according to claim 7 wherein the end effector connecting assembly further includes a yoke disposed adjacent the coupling member, the yoke being configured and dimensioned to retain a connection portion of an end effector therein.

9. A surgical instrument according to claim 7 wherein the coupling member is spring biased distally away from the housing.

10. A surgical instrumentation kit which comprises:
   a) a surgical instrument which includes:
      a handle which includes first and second relatively movable portions;
      an articulating arm extending from the handle, the articulating arm including a plurality of arm segments arranged in a series to form a flexible column;
      an end effector connecting assembly disposed at the distal end portion of the articulating arm, the end effector connecting assembly including a housing and a coupling member operatively connected to the distal end of the articulating arm and movable relative to the housing from a closed position to an open position, the coupling member being configured and dimensioned such that when disposed the closed position, the coupling member is capable of retaining a connection portion of an end effector and when disposed in the open position, the coupling member permits the removal or attachment of and end effector from the distal end of the articulating arm; and
   b) a plurality of interchangeable surgical tool end effectors each having a uniform connector portion for interchangeable engagement with the end effector connecting assembly of the surgical instrument.

11. A surgical instrumentation kit according to claim 10, wherein the plurality of interchangeable end effectors are selected from the group consisting of heart stabilizers and heart manipulators.

12. A surgical instrumentation kit according to claim 10, which further comprises a mounting assembly for mounting the surgical instrument to a base.

* * * * *